United States Patent
DeFreitas et al.

(10) Patent No.: US 8,532,745 B2
(45) Date of Patent: Sep. 10, 2013

(54) BREAST BIOPSY AND NEEDLE LOCALIZATION USING TOMOSYNTHESIS SYSTEMS

(75) Inventors: Kenneth F. DeFreitas, Patterson, NY (US); Ian Shaw, Yorktown Heights, NY (US); John Laviola, Orange, CT (US); Loren Thomas Niklason, Hillsborough, NC (US); Tao Wu, Brookfield, CT (US); Joseph L. Mark, Indianapolis, IN (US); Michael E. Miller, Trafalgar, IN (US); Jay A. Stein, Boston, MA (US); Andrew P. Smith, Lexington, MA (US)

(73) Assignee: Hologic, Inc., Bedford, MA (US)

(*) Notice: Subject to any disclaimer, the term of this patent is extended or adjusted under 35 U.S.C. 154(b) by 1833 days.

(21) Appl. No.: 11/707,587

(22) Filed: Feb. 15, 2007

(65) Prior Publication Data
US 2008/0045833 A1   Feb. 21, 2008

Related U.S. Application Data

(60) Provisional application No. 60/774,142, filed on Feb. 15, 2006.

(51) Int. Cl.
*A61B 5/05* (2006.01)

(52) U.S. Cl.
USPC ............ 600/427; 600/407; 600/425; 600/436

(58) Field of Classification Search
USPC ........................................................ 600/427
See application file for complete search history.

(56) References Cited

U.S. PATENT DOCUMENTS

| | | | |
|---|---|---|---|
| 4,821,727 | A | 4/1989 | Levene et al. |
| 5,078,142 | A | 1/1992 | Siczek et al. |
| 5,240,011 | A | 8/1993 | Assa |
| 5,289,520 | A | 2/1994 | Pellegrino et al. |
| 5,415,169 | A | 5/1995 | Siczek et al. |
| 5,426,685 | A | 6/1995 | Pellegrino et al. |
| 5,594,769 | A | 1/1997 | Pellegrino et al. |
| 5,609,152 | A | 3/1997 | Pellegrino et al. |
| 5,735,264 | A | 4/1998 | Siczek et al. |
| 5,769,086 | A | 6/1998 | Ritchart et al. |
| 5,803,912 | A | 9/1998 | Siczek et al. |
| 6,022,325 | A | 2/2000 | Siczek et al. |
| 6,101,236 | A * | 8/2000 | Wang et al. ................ 378/4 |
| 6,459,925 | B1 | 10/2002 | Nields et al. |
| 6,620,111 | B2 | 9/2003 | Stephens et al. |
| 6,626,849 | B2 | 9/2003 | Huitema et al. |

(Continued)

FOREIGN PATENT DOCUMENTS

| | | |
|---|---|---|
| WO | WO 00/51484 | 9/2000 |
| WO | WO2005/110230 A1 | 11/2005 |

(Continued)

OTHER PUBLICATIONS

"Filtered Back Projection," (NYGREN) published May 8, 2007; URL: http://web.archive.org/web/19991010131715/http://www.owlnet.rice.edu/~elec539/Projects97/cult/node2.html.

(Continued)

*Primary Examiner* — Unsu Jung
*Assistant Examiner* — Saurel J Selkin
(74) *Attorney, Agent, or Firm* — Cooper & Dunham, LLP

(57) ABSTRACT

Methods, devices, apparatuses and systems are disclosed for performing mammography, such as utilizing tomosynthesis in combination with breast biopsy.

32 Claims, 17 Drawing Sheets

System showing tomo scan skipping exposures at angles that would cause artifacts of stage in the image

(56) References Cited

U.S. PATENT DOCUMENTS

| | | | |
|---|---|---|---|
| 6,638,235 B2 | 10/2003 | Miller et al. | |
| 6,758,824 B1 | 7/2004 | Miller et al. | |
| 7,123,684 B2 | 10/2006 | Jing et al. | |
| 2001/0038681 A1 | 11/2001 | Stanton et al. | |
| 2003/0018272 A1 | 1/2003 | Treado et al. | |
| 2003/0073895 A1 | 4/2003 | Nields et al. | |
| 2004/0081273 A1* | 4/2004 | Ning | 378/37 |
| 2004/0171986 A1 | 9/2004 | Tremaglio, Jr. et al. | |
| 2004/0267157 A1 | 12/2004 | Miller et al. | |
| 2005/0049521 A1 | 3/2005 | Miller et al. | |
| 2005/0113681 A1 | 5/2005 | DeFreitas et al. | |
| 2005/0113715 A1 | 5/2005 | Schwindt et al. | |
| 2006/0030784 A1 | 2/2006 | Miller et al. | |
| 2006/0098855 A1 | 5/2006 | Gkanatsios et al. | |
| 2006/0129062 A1 | 6/2006 | Nicoson et al. | |
| 2006/0155209 A1 | 7/2006 | Miller et al. | |
| 2007/0225600 A1 | 9/2007 | Weibrecht et al. | |
| 2007/0263765 A1* | 11/2007 | Wu | 378/37 |

FOREIGN PATENT DOCUMENTS

| | | |
|---|---|---|
| WO | WO2005/112767 A1 | 12/2005 |
| WO | WO2006/055830 | 5/2006 |
| WO | WO2006/058160 | 6/2006 |

OTHER PUBLICATIONS

Feb. 20, 2008 International Search Report and Written Opinion in connection with corresponding International patent application No. PCT/US2007/04006.

Mar. 23, 2009 European search report in connection with counterpart European Patent Application No. 07 75 0818.

* cited by examiner

System showing side lateral needle access to area of interest

System showing front needle access to area of interest

System showing tangential needle access, and opening in compression paddle to allow needle to enter the breast Paddle with access hole System showing asymmetric tomo scan to avoid shadowing the gun stage System showing tomo scan skipping exposures at angles that would cause artifacts of stage in the image Figure 6 Illustration of biopsy needle with two radio-opaque tips and transparent body Figure 7 Illustration of biopsy needle with two radio-opaque tips and transparent body embedded with metallic stiffening rods Figure 8 Illustration of biopsy needle with two radio-opaque tips and a coaxial layer, one of which is radio-opaque and the other radio-lucent.

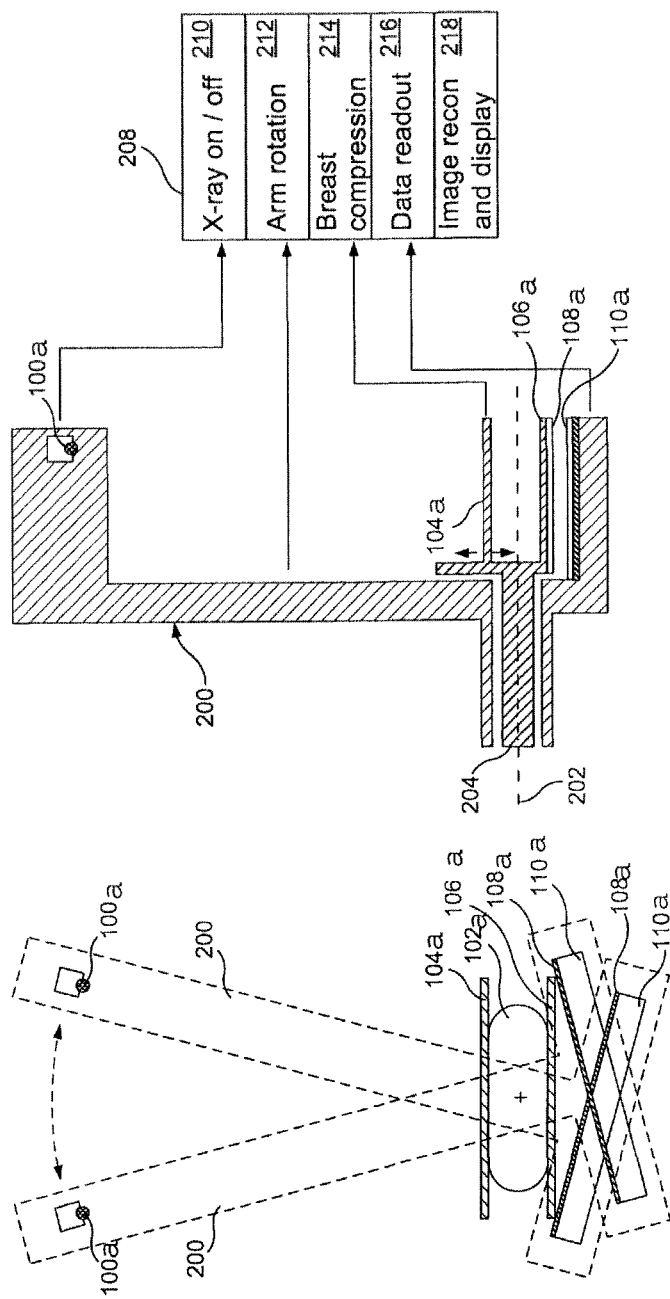

BREAST BIOPSY AND NEEDLE LOCALIZATION USING TOMOSYNTHESIS SYSTEMS

CROSS-REFERENCE TO RELATED APPLICATIONS

This application claims Priority from Provisional Application 60/774,142 filed Feb. 15, 2006 now expired.

BACKGROUND AND SUMMARY OF THE DISCLOSURE

Mammography is a well-established method of breast imaging. Using mammograms of the breast, radiologists identify areas suspicious of pathologies. Further identification, such as the determination of cancer is usually done through the taking of a breast biopsy. This is done in several ways. One way is to use mammography to place a wire or needle into the breast, marking the suspected pathology's location. The patient then undergoes an open surgical procedure, and the surgeon can remove tissue from the suspicious area marked by the wire or needle. This is an open surgical biopsy. Another method is known as stereotactic breast biopsy. In this method, using image guidance, a hollow needle is inserted into the breast, and a tissue sample is taken from the area of interest, without a separate surgical procedure. As stated above both methods require some method of localization of the area of interest and a method to direct a wire or needle into the breast so it resides at the already identified area of interest's location.

This patent disclosure covers methods of wire and/or needle guidance into the breast using breast tomosynthesis imaging technology. It covers both upright and prone biopsy equipment.

Tomosynthesis (tomo) is a method of performing three dimensional (3D) breast x-ray imaging. It generates images of cross sectional slices through a compressed breast, and also is used to identify breast pathologies. One of the advantages of tomosynthesis is that the images are three-dimensional, so that once an area of interest is identified in an image, its exact 3D coordinate in the breast can be calculated or estimated, e.g. from the x, y coordinate in the image of a slice and from the z, or depth, coordinate given by the image slice depth location. Another advantage of tomosynthesis is its ability to provide high contrast visibility of objects by the suppression of images from objects at different heights in the breast. Because of its superior contrast visibility, it is expected that there will be pathologies seen on the tomo images that will not be visible using standard x-ray mammography or stereotactic devices or using ultrasound or even MRI or other methods currently employed to provide guidance to the insertion of wires and needles to the location of an identified area of interest. For this reason, it is desired to develop localization methods using tomosynthesis systems that utilize tomosynthesis' natural 3D localization abilities.

This patent disclosure addresses both systems and methods for tomosynthesis imaging, and devices and methods for needle and wire localization using tomosynthesis imaging systems. In one non-limiting example, the new approach described in this patent disclosure is based on conventional tomosynthesis designs, e.g, as described in U.S. patent application Ser. No. 10/305,480, filed Nov. 27, 2002, now U.S. Pat. No. 7,123,684, issued Oct. 17, 2006, U.S. patent application Ser. No. 10/723,486, filed Nov. 26, 2003, now U.S. Pat. No. 7,831,296 issued Nov. 9, 2010, U.S. Provisional Patent Application Ser. No. 60/628,516, filed Nov. 15, 2004, International PCT Application Serial No. PCT/US2005/0491941, filed Nov. 15, 2005, published as WO/2006/055830 on May 26, 2006, U.S. Provisional Patent Application Ser. No. 60/631,296, filed Nov. 26, 2004, and International PCT Application Serial No. PCT/US2005/042613, filed Nov. 23, 2005, published as WO/2006/058160 on Jun. 1, 2006, which are hereby incorporated by reference. Typically, the breast is compressed between a breast platform and a compression paddle. The paddle may be one of the standard paddles used for screening mammography, or one with holes and guide marks used for needle localization or biopsy procedures with conventional mammography equipment, e.g, as described in U.S. Pat. No. 5,078,142 filed Nov. 21, 1989, U.S. Pat. No. 5,240,011 filed Nov. 27, 1991, U.S. Pat. No. 5,415,169 filed Feb. 17, 1993, U.S. Pat. No. 5,735,264 filed Jun. 7, 1995, U.S. Pat. No. 5,803,912 filed Apr. 25, 1995, U.S. Pat. No. 6,022,325 filed Sep. 4, 1998, U.S. Pat. No. 5,289,520 filed Oct. 6, 1992, U.S. Pat. No. 5,426,685 filed Jan. 24, 1994, U.S. Pat. No. 5,594,769 filed May 9, 1995, and U.S. Pat. No. 5,609,152 filed Feb. 15, 1995, which are hereby incorporated by reference, and as used in the prone or upright needle biopsy devices commercially available from the Lorad Division of Flologic, Inc, of Bedford, Mass. The x-ray tube is mechanically designed so that it moves along a path that images the breast from differing angles, making a sequence of exposures at differing locations along the path. A digital x-ray image receptor acquires the images. The detector can be stationary during the scan, or it can move during the scan such as if it was mounted on a c-arm connected with the x-ray tube or is otherwise connected to move in sync with the x-ray tube, though not necessarily through the same angle. The entire system can be oriented so that the patient is either upright or lying on a table with her breast pendulant and protruding through a hole in the table and positioned properly on the detector to access the area of interest as needed. One system design would be using a relatively small field of view, such as approximately 5×5 cm. This would correspond to developing a tomosynthesis biopsy system with similar field of view to standard prone table stereo localization systems. However, another way disclosed here, which differentiates a tomo biopsy system from conventional stereo localization system, is to use a significantly larger detector field of view. In one example of an embodiment the field of view can be at least 10×10 cm, in another at least 20×25 cm, in another approximately 24×29 cm.

Localization of an area of interest can start with breast acquisition carried out in a standard way used in breast tomosynthesis. The data is reconstructed, and reviewed. The area of interest is identified either on the reconstructed images of slices, or in the raw projection images. The 3D coordinates of the area of interest can be computed or estimated from the identification of the area of interest on the images.

Once the 3D location of the area of interest is calculated, known methods of directing needles and wires to that location can be used.

There might be some differences in tomo scans during biopsy procedures from screening mammography. The dose might be higher, to get lower noise images. The angular range might be wider or shallower, and the number of projections might be larger or smaller. One might want a wider angle, for example, to get higher precision depth discrimination. One might also want higher resolution for these scans, compared to conventional tomo screening. This could be accomplished through the use of smaller pixel sizes.

A biopsy system used with a tomosynthesis system can include a needle gun assembly with motorized or non-motorized stage that can direct a needle to a specific 3D coordinate in the breast. This stage may be swung or otherwise moved out of the way of the acquisition system during the initial tomosynthesis scan, so that if desired it does not shadow or interfere with the visualization of the breast or breast area of interest.

Following the tomo scan and the identification of the 3D area of interest location, the stage is moved into place. The needle is moved to the 3D coordinate previously identified. The needle may access in the breast via a left or right lateral access (e.g. with the needle roughly parallel to the compression paddle and the patient's chest wall), or it could access the breast with the needle roughly normal to the compression paddle, through an opening in the compression paddle. Or, the needle may enter the breast at an angle between the normal and parallel paths (in relation to the compression paddle and detector) through a hole in the breast compression paddle. It may also come from the front of the breast, directing the needle rearwards towards the chest wall. It can also come from between the paddle and the breast platform but at an angle rather than through the hole in the paddle.

The biopsy system should be capable of working with the tomosynthesis system in all orientations of the tomosynthesis system, including, but not limited to, CC, MLO, and ML and LM imaging orientations. These systems can rotate 360° around the breast and take images from any angle.

Standard techniques of breast biopsy typically involve verification of the needle's location before tissue sampling, known as pre- and post-fire verification. In pre-fire, the needle is inserted into the breast approximately 2 cm short of the center of the area of interest and x-ray exposures are made and images are generated and viewed to verify proper pre-fire needle location relative to the area of interest before tissue sampling. In post-fire, at least one additional exposure is made and the resulting image is viewed to verify proper needle location relative to the area of interest after the firing of the needle and before the tissue is sampled.

These verification images can be images from tomosynthesis scans, or they can be stereo x-ray pairs or individual images. The tomosynthesis scans can be done with different angular ranges and different number of projections and a different dose from conventional tomosynthesis imaging.

Post-fire needle verification can be accomplished in a variety of ways, which may depend on whether the needle access was lateral or tangential. One challenge arises from the fact that the gun and stage and needle are generally radio-opaque and can contribute artifacts to the images if not properly dealt with.

With tangential access, there may be an angular range where the gun and stage shadow the breast. Lateral access may not have the problem of the gun stage in the field of view, but it can have the needle in the field of view, and there might be other mechanics that if imaged can create image artifacts. In general, x-rays from angles that shadow the gun and stage are less useful. Solutions to this problem in accordance with the new approach disclosed in this patent specification include:

a. Development of needle and other sheathing materials that are sufficiently radiolucent that they will not create significant image artifacts. Possible materials are plastics, ceramics, glasses, carbon tubes, and low atomic number metals and other materials. If these materials are used, they can be marked with fiducial markings such as radio-opaque rings or dots allowing visibility in the tomosynthesis images so they can be differentiated from breast tissue or breast area of interest. Alternately, a needle can be used where only the tip (last 1-3 cm) is radiolucent and rest of the needle is radio-opaque.

b. Scanning through angles that do not shadow these objects. This can entail an asymmetric scan geometry, whereby all or an important part of the x-ray beam path does not pass through the needle or other radio-opaque parts. An example is scanning to just one side of the needle.

c. Scanning over a large range, and generally or always avoiding x-ray exposures when the stage or other radio-opaque parts shadow the breast, area of interest or image receptor. Alternatively, x-ray imaging can be done even in angular areas with this shadow problem, but these exposures can be eliminated from viewing or reconstruction, either automatically or through manual elimination via a user interface. Another alternate method involves artifact suppression algorithms used during reconstruction, as in known in tomosynthesis and CT scanning.

d. Stereotactic imaging. Conventional stereotactic imaging involves using a pair of x-ray images at, for example, ±15° to the normal to the compression paddle. This geometry involves sufficiently large angles to typically avoid the stage shadows on the image receptor. A tomo system can be used to take tomo projection images at angles that avoid undesirable shadows at relevant parts of the images.

e. Scan angle changes. A larger scan angle than used in conventional tomo imaging can better avoid artifacts from the stage.

f. Bringing the needle to a fixed distance from the lesion. An image can then be taken that does not obscure the area of interest, and the proper distance between needle and area of interest can be verified from imaging. The needle can then be advanced into the correct location within the area of interest based on information from the tomo or conventional imaging while the needle is spaced from the area of interest.

g. In many if not most cases the projection images and perhaps the reconstructed images of breast slices will contain at some location an image of the needle. The needle image can create artifacts in reconstructed images, which can be removed via artifact reduction algorithms as in known in conventional tomosynthesis and CT imaging. One algorithm can involve skipping projection images with extensive shadowing in the projections. Another algorithm can involve segmenting out the needle and other high contrast objects and avoiding reconstruction using these pixels, as has been used in CT and other imaging. Other alternatives include viewing the projection images, which can have images of the needles but no other significant artifacts.

The examples of embodiments disclosed in this patent specification can include user interfaces to mark the area of interest location on either the projection tomo images or the reconstructed tomo images of breast slices. Signals directing the needle to the correct location in the breast can be generated automatically based on identifying the location of the area of interest in the images, or the coordinates of the area of interest can be displayed and the needle can be guided to the appropriate location under manual control.

For the pre and post fire images, a facility can be provided to mark the previously identified area of interest location on the current images. This can help visualization of proper needle placement, in case the area of interest becomes harder to see because it has been removed or in case the needle creates large artifacts. The orientation of the needle relative to this mark can provide assurance as to proper location placement.

The 3D nature of the tomosynthesis images allows for calculation of the 3D volume of the area of interest, once it has been identified on the tomosynthesis projections or reconstructed images of slices. This can be part of the display and used to help verify that the correct lesion has been targeted.

BRIEF DESCRIPTION OF THE DRAWINGS

FIGS. 12-14 illustrate a tomosynthesis system and its operation.

DETAILED DESCRIPTION OF EXAMPLES OF PREFERRED EMBODIMENTS

Figure 1:
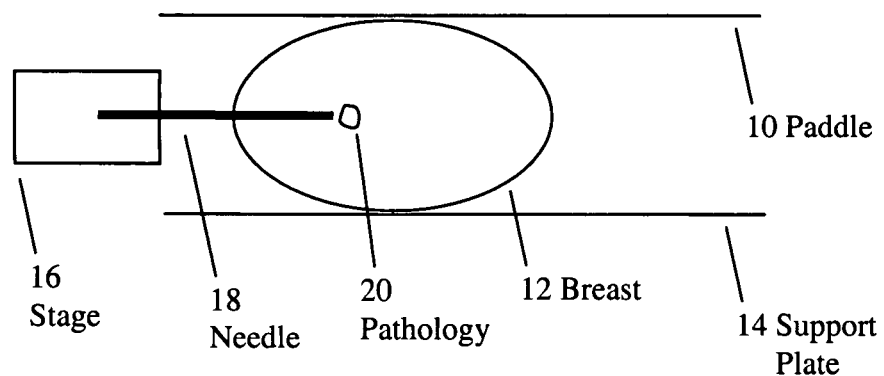
FIGS. 1-5 illustrate various ways of positioning a biopsy needle relative to a breast and imaging positions of an x-ray source and an image plane for reducing undesirable image artifact due to the presence of the needle or other radio-opaque material.

FIG. 1 illustrates lateral needle access, where a breast compression paddle 10 and a breast support plate 14 can be a part of an otherwise known tomosynthesis system such as described in the co-pending patent applications identified above and incorporated by reference in this patent specification, and a biopsy needle stage 16 and a needle 18 such as used, for example, in the patents identified above that pertain to prone biopsy. For clarity, the rest of the tomosynthesis system and other parts of the biopsy apparatus are not shown in this FIG. 1, and a detailed discussion of the basic aspects of tomosynthesis is not included herein. The reader is referred to the references cited herein for such discussions. For example, image reconstruction can be performed using filtered back projection (for rapid speed of reconstruction) and/or artifact reduction methods (such as ordered statistics back projection), as disclosed, for example, in U.S. Patent Application Publication No. 2002/0113681, the entire contents of which are incorporated by reference herein.

A patient's breast 12 is compressed between paddle 10 and support plate 14 and a needle biopsy stage 16 has been used to position the tip of a biopsy needle 18 near an area of interest 20 in breast 12. In this example needle 18 enters the breast 12 generally laterally, i.e. along the plane of support plate 14 and along the chest wall of the patient, and from the left as seen in the drawing. Of course, the needle 18 can enter instead from the right, and need not be exactly parallel to support plate 14 or to the chest wall, but can be at any angle thereto that the health professional doing the needle biopsy finds suitable for the particular patient or area of interest location. As described above, the location of area of interest 20 has been determined based on tomosynthesis images that can be tomo projection images and/or tomo reconstructed slice images. In FIG. 1, the patient's chest is behind the illustrated structure and is generally along the plane of the sheet. If upright biopsy is used, the patient's chest wall would be generally vertical; if a prone biopsy table is used, the patient's chest wall would be generally horizontal.

Figure 2:
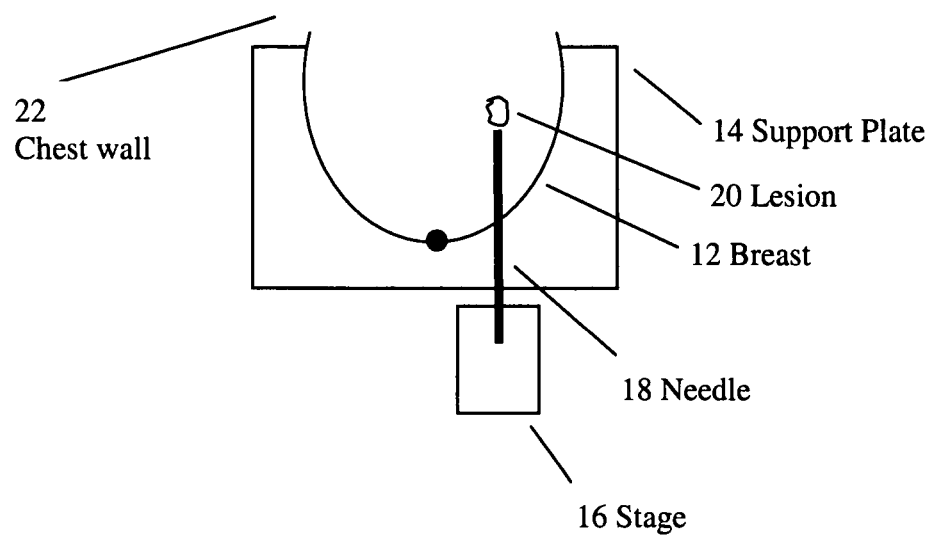

FIG. 2 illustrates frontal needle access in which needle 18 accesses area of interest 20 from the front of breast 12, in a direction generally along the plane of support plate 14 and normal to chest wall 22 of the patient. Again, the needle 18 direction need not be exactly parallel to support plate 14 or normal to chest wall 22, but can be at any convenient angle thereto that would allow the tip of needle 18 to reach area of interest 20 generally from the front of the breast 12, at either side of the nipple. In FIG. 2 the patient's chest wall 22 is generally normal to the sheet.

Figures 3A, 3B:
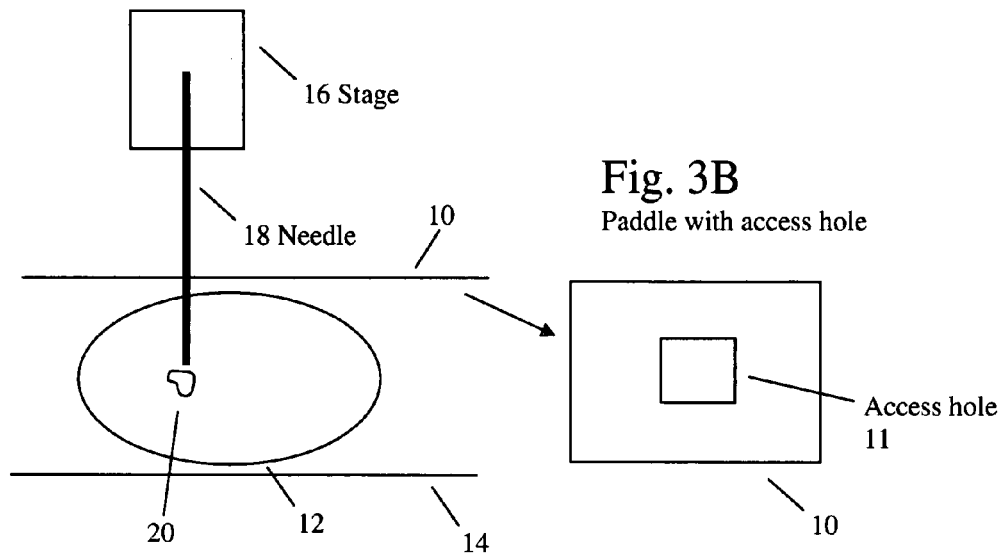

FIG. 3a illustrates tangential needle access, where a breast compression paddle 10 has, as seen in FIG. 3b, one or more needle access holes 11. FIG. 3a illustrates breast compression paddle 10, breast 12 and support plate 14 in a view similar to that of FIG. 1, but a needle stage 16 and needle 18 at a position above the breast. Needle 18 accesses area of interest 20 in a direction generally normal to support plate 14 and along the chest wall (not shown) of the patient. Again, needle 18 need not be at the angles shown but may be at any angle that the health professional doing the biopsy finds suitable.

Figure 4:
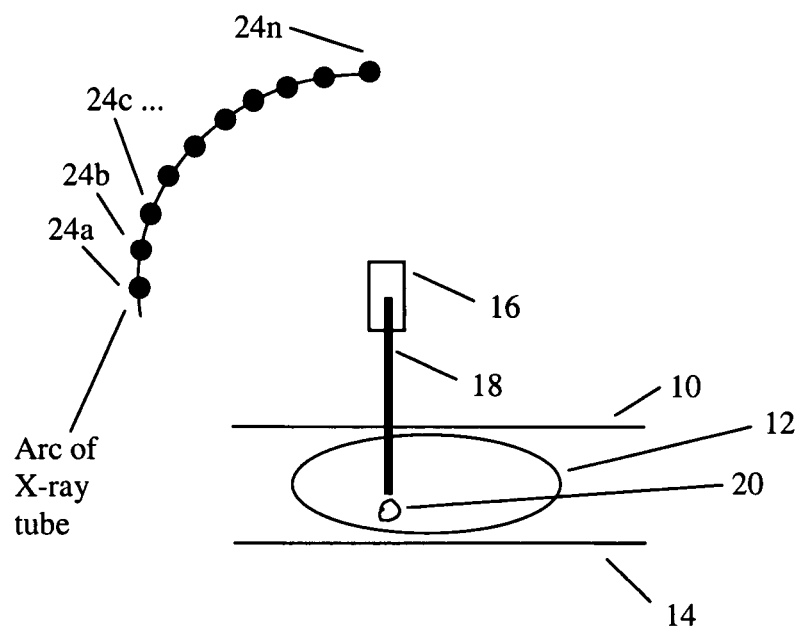

FIG. 4 illustrates one type of a tomo scan that can be used to reduce undesirable image artifacts due to the presence of a biopsy needle 18 and possibly other radio-opaque materials. While FIG. 4 illustrates tangential needle access similar to that of FIG. 3, the principles discussed below in connection with FIGS. 4 and 5 apply to any other type of access to area of interest 20. FIG. 4 illustrates positions 24a, 24b, . . . , 24n of an x-ray tube (not shown) from which the tube emits x-ray beams for taking tomo projection images. While positions 24a-24n are illustrated as being along an arcuate path, they can be along a differently shaped path, and scanning can start from either end of the path, or from an intermediate positions along the path. As evident from FIG. 4, it is likely that at some positions of the scan, needle stage 16 would obscure at least a significant part of the imaging x-ray beam and the resulting projection image is likely to have significant and probably unacceptable artifacts.

Figure 5:
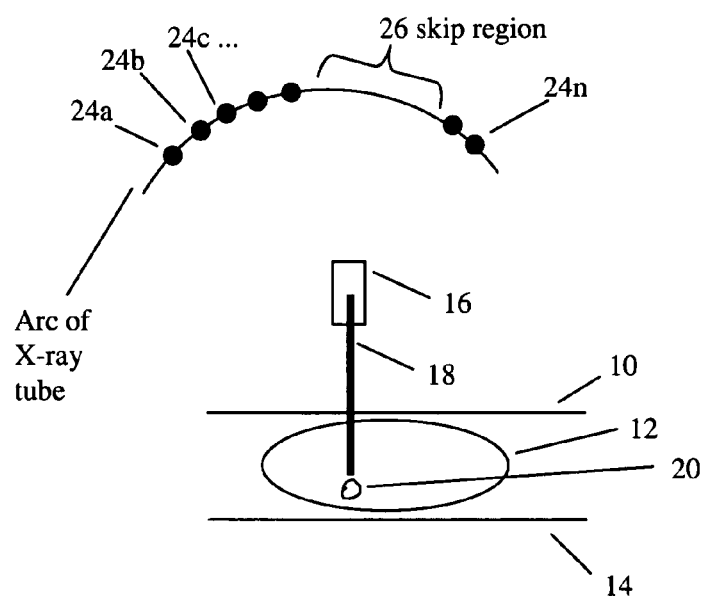

FIG. 5 is otherwise similar to FIG. 4 but illustrates a gap region 26 in the path of x-ray tube positions 24a-24n. No x-ray tomo exposures are taken from positions in this gap region 26. Exposures are taken from positions outside this region to minimize or at least significantly reduce the extent to which the needle stage 16 and any other x-ray opaque materials affect the imaging x-ray beams and thus reduce undesirable artifacts in the images relative to images that could have been obtained with exposures taken from positions in gap 26. Sufficient tomo projection images can be taken from positions outside gap 26 from which acceptable tomo reconstructed images of breast slices can be computed to localize needle 18 relative to area of interest 20. Gap 26 can be at an end of the path of positions 24a-24n or it can be intermediate positions 24a-24n. Different x-ray dose can be used for different ones of positions 24a-24n, e.g. less dose for exposure positions in which radio-opaque materials in the path of the x-ray beam are likely to generate more undesirable artifacts, and greater dose for positions in which such material are less likely to produce such artifacts. It is possible to take exposures even from positions in gap 26, preferably at low x-ray dose, but not use the resulting projection images for reconstructing tomo images of breast slices.

During the x-ray tomo exposure, metallic breast biopsy needles can obstruct the sampled lesion or cause other undesirable artifacts such as, for example, streaking artifacts in reconstructed tomosynthesis images. This is especially acute where the sampled lesions are calcifications. This obstruction can reduce the accuracy of biopsy. Embodiments of the present disclosure include a needle design that allows for better visibility of the sampled lesion.

Figure 6:
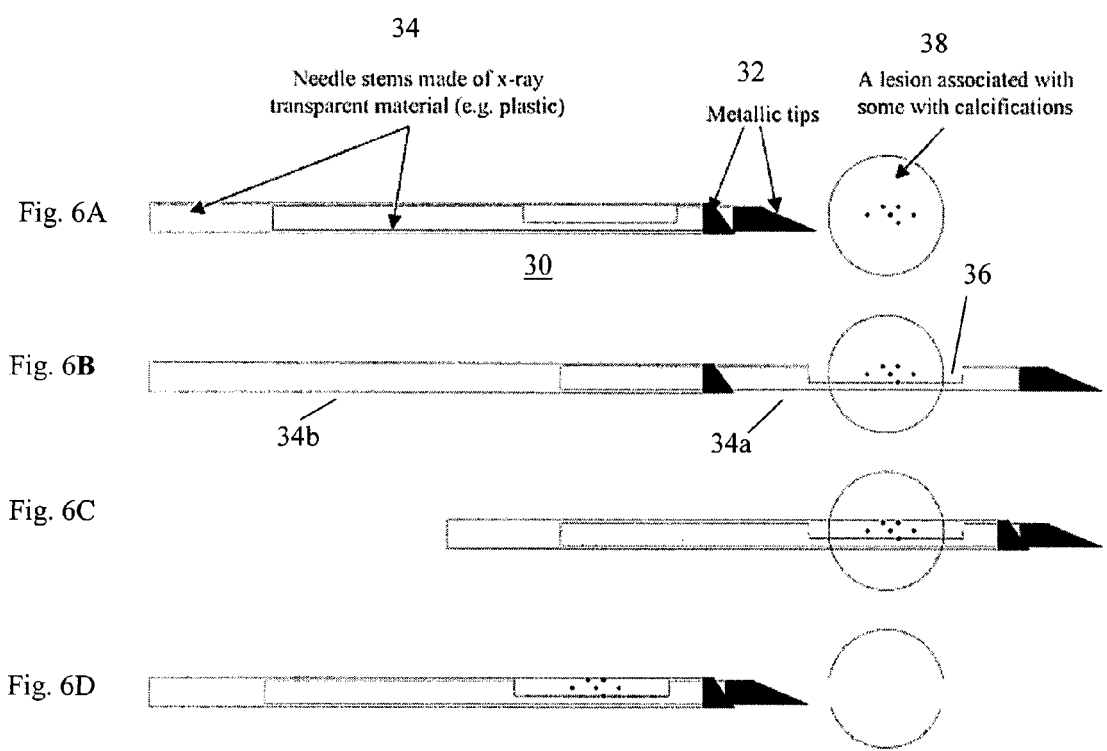
FIGS. 6A-6D, 7A-7E, 8A-8E, 9 and 11 illustrate various biopsy sampling needle designs for reducing undesirable image artifacts.
Figure 7:
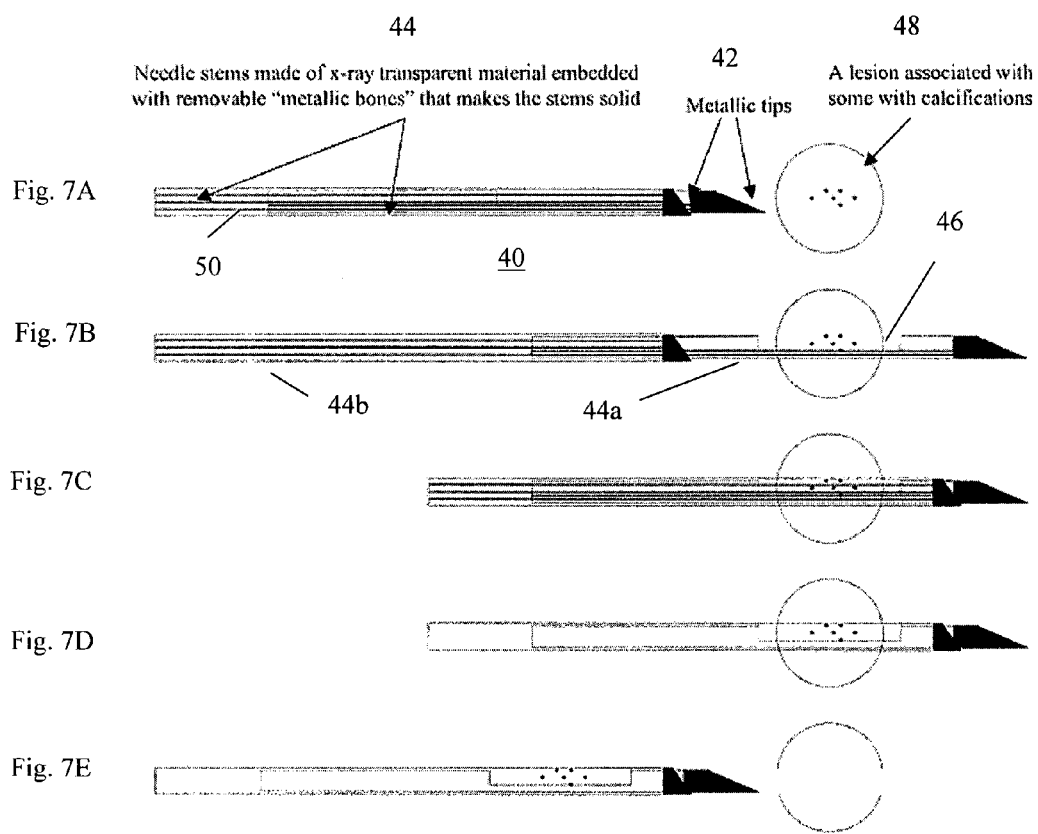
Figure 8:
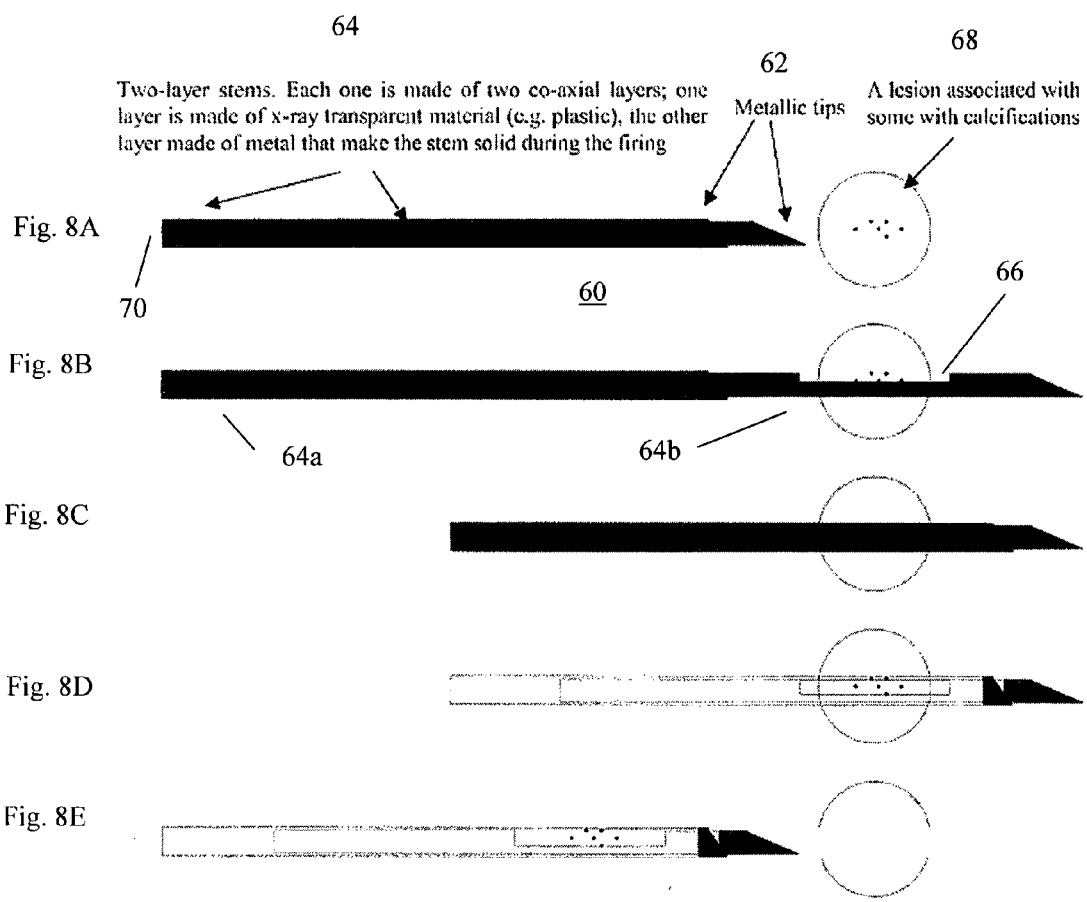

Several embodiments of such needles are shown in FIGS. 6-8. Here, x-ray transparent material is used in the construction of the stem of the needle to a significant extent so the sampled lesions can be seen more clearly when imaged with tomosynthesis or 2D mammography. The needle stem should still be solid enough to cut the tissue and the lesion. Of course, the x-ray transparent material need not be perfectly transparent but only sufficiently transparent to minimize or at least significantly reduce undesired image artifacts as compared with the use of metallic needles without such material. The term "x-ray transparent" is used in this sense in this patent disclosure.

FIGS. 6A-6D illustrates the use of a breast biopsy needle with an x-ray transparent body according to embodiments of the present disclosure. The needle 30 consists of two metallic tips 32 for cutting the tissue and lesion 38, and two needle stems 34 made of x-ray transparent material so as not to block x-rays. Because the needle stems 34 are x-ray transparent, the position of the needles may be determined by the position of the needle tips 32 in x-ray images and the known needle geometry. FIG. 6A illustrates the needle 30 prior to its firing, The relative location of the needle and the lesion 38 are confirmed using x-ray tomosynthesis (or 2D x-ray mammography). FIG. 6B illustrates that one of the two needle stems 34 may have a notch 36. The notched needle stem 34a may be within the lumen or cannula of the un-notched needle stem 34b. The notched needle stem 34a may be fired from the un-notched needle stem 34b such that the notch is placed in proximity to the lesion 38. FIG. 6C illustrates that the un-notched stem 34b may be pushed to close around the notched stem 34a thereby cutting and trapping the lesion 38, or at least a part thereof, within the notch 36 and the cannula of the un-notched stem 34b. Tomosynthesis or 2D mammography may then be used to confirm the position of the lesion 38 within the notch 36 and the cannula of the un-notched stem 34b. FIG. 6D illustrates that the needle may be removed from the patient with the trapped lesion 38. Tomosynthesis or 2D mammography may then be used to confirm that the lesion 38 has been correctly sampled.

FIGS. 7A-7E illustrate the use of a breast biopsy needle with an x-ray transparent body stiffened with metal according to another embodiment of the present disclosure. The needle 40 comprises two metallic tips 42 (to cut the tissue and lesion 48), and two needle stems 44 made of x-ray transparent material (so as not to block or scatter x-rays excessively) and removable solid metallic wires or ribs 50 to enhance the structural integrity of the needle stems during the firing. The wires or ribs 50 can be removed from the stems, after firing, to allow the needle stems 44 to be x-ray transparent and the taking of x-ray images after the wires or ribs 50 have been withdrawn. As seen in FIG. 7A, before firing the needle 40, the relative location of the needle 40 and the lesion 48 may be confirmed using tomosynthesis or 2D mammography. As seen in FIG. 7B, a notched needle stem 44a may be fired from an un-notched needle stem 44b. As seen in FIG. 7C, the un-notched needle stem 44b may be pushed to the notched needle stem 44a so as to cut and trap the lesion 48 between the notch 46 of the notched needle stem 44a and the un-notched needle stem 44b. As seen in FIG. 7D, the metallic wires 50 can be removed form the needle stems 44 prior to performing tomosynthesis or 2D mammography to confirm the location of the lesion 48. As seen in FIG. 7E, the needle 40 may be removed from the patient with the trapped lesion 48. Tomosynthesis or 2D mammography may then be used to confirm that the lesion 48 has been correctly sampled.

FIGS. 8A-8E illustrate another embodiment of a new breast biopsy needle that comprises two coaxial bodies each having an x-ray transparent (e.g. plastic) layer and an x-ray opaque (e.g. metal) layer that adds mechanical strength or stiffness but can be withdrawn, if desired, after the needle is in place in the breast but before x-ray images are taken. As seen in FIG. 8A, needle 60 is inserted into the breast until its cutting tips 62 are close to but spaced from suspected lesion 68. At this time, the relative locations of the needle and the lesion can be confirmed by taking tomosynthesis or 2d mammography images. Then, as seen in FIG. 8B, the notched stylet 64b (the notch shown as 66) of the needle can be fired into lesion 68 to sample it and, as seen in FIG. 8C the cannula 64a can be pushed in to slice the lesion or at least a part of it into the notch. Then the radio-opaque metal layers can be withdrawn from each of the cannula and the stylet to leave the x-ray transparent structure seen in FIG. 8D (except for its cutting tips 62). At this time, post-fire tomosynthesis or 2D mammography images can be taken to confirm that the lesion or a part of it is in the notch. Because of the use of x-ray transparent material at the lesion at this time, the post-fire images are unlikely to suffer from undesirable artifacts. The core system can then be pulled back with the lesion sample, e.g. to the position illustrated in FIG. 8E.

Figure 9:
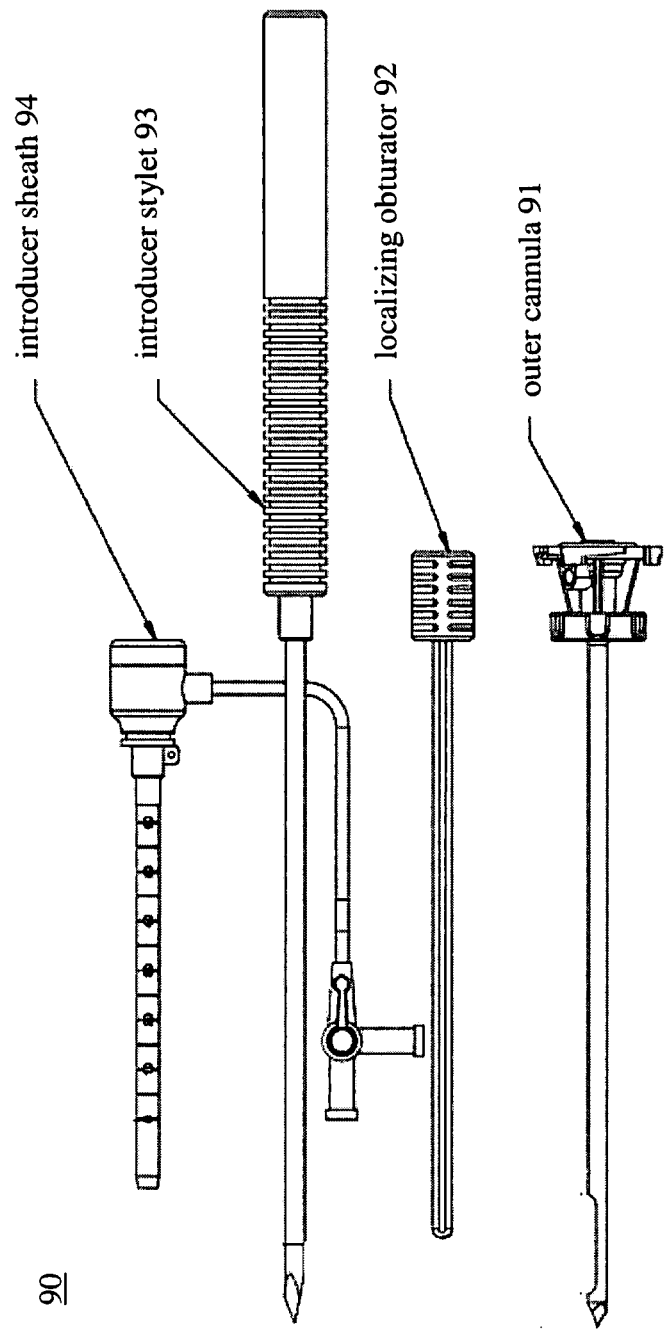

FIG. 9 illustrate another example of a new breast biopsy needle. Biopsy needle 90 is configured as "tube-within-a-tube" cutting device and includes an outer cannula 91, an inner cannula (or localizing obturator) 92, an introducer stylet 93 and an introducer sheath 94. In addition, the outer cannula 91, localizing obturator 92, introducer stylet 93 and introducer sheath 94 can be mounted to a handpiece (not shown) or an attachment (not shown) which is in turn coupled to a support fixture or positioning device for moving the biopsy needle to a desired position. The outer cannula 91 defines an outer lumen and terminates in a tip which is preferably a trocar tip that can be used to penetrate the patient's skin. The localizing obturator 92 fits concentrically within the outer cannula 91. The localizing obturator 92 can be driven by a rotary motor and a reciprocating motor drive to translate the localizing obturator 92 axially within the outer cannula 91, while rotating the localizing obturator 92 about its longitudinal axis (or the localizing obturator 92 can be rotated and/or translated manually). Alternatively, the introducer stylet 93 which is inserted in the annular introducer sheath 94 can be inserted. In this example, the introducer stylet 93 and/or sheath 94 can be radiolucent with a radio-opaque band at a distal end thereof.

Additional examples of breast biopsy needles are disclosed in U.S. Pat. Nos. 6,638,235, 6,758,824, 6,620,111 and 6,626,849 and U.S. Publications Nos. 2006/0155209 A1, 2006/0129062 A1, 2006/0030784 A1, 2005/0113715 A1, 2005/0049521 A1, and 2004/0267157 A1, the entire contents of which are incorporated herein by reference.

Thus, in one aspect this patent specification discloses a method and a system in which tomosynthesis reconstructed images of slices of a patient's breast and/or tomosynthesis projection images of the breast are used to (1) identify the location of a suspected area of interest in the breast, (2) guide needle biopsy of the area of interest, (3) confirm pre-fire position of the needle relative to the area of interest, and/or (4) confirm post-fire position of the needle relative to the area of interest. One unique benefit of this approach is with respect to suspected pathologies that can be seen or assessed better in tomosynthesis images than in conventional mammograms or in conventional ultrasound images of breast tissue. The method and system involve taking a series of tomosynthesis projection images at respective different angles of the imaging x-ray beam relative to the breast, for example in the manner disclosed in said patent applications that are incorporated by reference in this patent specification. The information from these projection images is reconstructed into images of slices through the breast, which may represent slices of selected thickness and selected angles relative to the breast platform or the imaging plane(s) of the projection images. Typically but not necessarily the reconstructed images represent slices that are parallel to the breast platform and thus to the plane of a conventional mammogram. These images are used to identify the location of the area of interest in the breast in three dimensions, for example by having the health professional point to the location of the area of interest in one or more images and using the system to compute the 3D coordinates of the location in a manner similar to that used in said biopsy system patents identified above and incorporated by reference in this patent specification, or in a different manner, such as by pointing to the area of interest in a reconstructed slice image to thereby identify the location of the area of interest in two dimensions in the plane of the slice and to provide the third dimension from knowledge of the depth of the slice in the breast. This 3D information of the area of interest location can be used together with information regarding a geometrical relationship between the equipment in which the breast of compressed and immobilized to determine the direction and extent of biopsy needle motion executed by a needle stage in a manner similar to that disclosed in said patents incorporated by reference herein, to position the needle, to sample the area of interest and to confirm pre-fire and post-fire locations of the needle relative to the area of interest.

In order to reduce undesirable artifacts in the x-ray images due to the presence of radio-opaque objects such as the biopsy needle in the imaging x-ray beam, the method and system disclosed here employ new approaches either singly or in combinations or subcombinations with each other. A first new approach in this respect pertains to selection of tomosynthesis images and involves taking projection tomosynthesis images only at angles in which the radio-opaque objects are not in the imaging x-ray beam or, if they are in the beam, their effect in the image is significantly less than it would have been for other possible beam angles. This may involve not taking projection images at angles that would produce more undesirable artifacts and/or taking such projection images but not using them in reconstructing slice images. A second new approach that can be used instead of or in addition to the first one is to carry out post-processing of the tomo images to reduce artifact therein due to the presence of radio-opaque objects in the beam. This can involve processing of the reconstructed slice image, e.g. by using streak artifact removal algorithms similar to those conventionally used in CT (computerized tomography) technology, and/or image processing of the tomo projection images to remove or reduce such artifacts. A third new approach that can be used instead of one or more of the first and second, or together with one or both of the first and second, is to use biopsy equipment that reduces or avoids such image artifacts, e.g. a biopsy needle that is made at least partly of a material that is significantly more x-ray transparent than conventional biopsy needles. A needle made of such material can be used as is for insertion into the breast and for tissue sampling, or it may be stiffened by portions of an x-ray opaque material such as metal that are used for insertion and/or tissue sampling but are withdrawn from the breast or at least from the immediate vicinity of the area of interest before pre-fire and/or post-fire x-ray images can be taken to thereby avoid the image artifacts that such metal would cause if not withdrawn. As one example, such stiffening portions can be in the form of pins or ribs inside a cannula. As another example, they can be sleeves coaxial with a cannula and/or a stylet. Other examples of stiffening portions that are withdrawn before pre-fire and/or post fire imaging also are contemplated.

Figure 10:
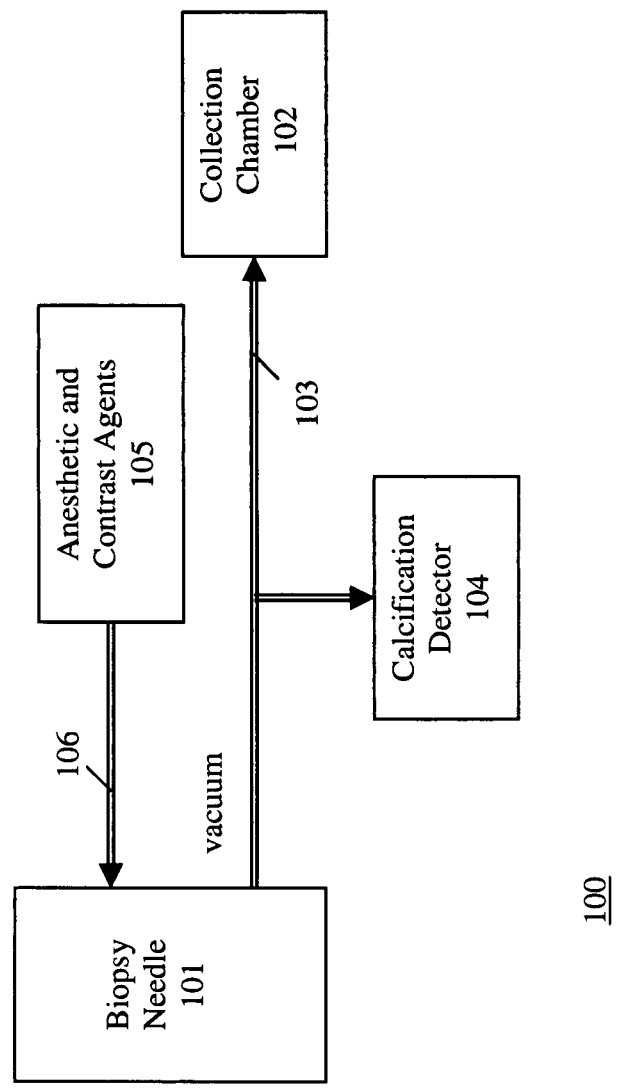
FIG. 10 shows a block diagram of a system with additional optional features.

Additional features can be added. For example, in the system 100 shown in FIG. 10, a calcification detector 104 is added in a sample delivery path 103 between a biopsy needle 101 and a collection chamber (or filter) 102. The sample delivery path 103 typically includes a tube or other channel for delivery of the extracted sample to the collection filter 102. The calcification detector 104 can be coupled to the sample delivery path 103 to determine whether the samples include calcifications and estimate an amount of the calcifications. The calcification detector 104 can include, as an example, an x-ray source and detector for imaging the samples passing through the sample delivery path 103, and a CAD (computer aided diagnosis) component configured to detect and count the number of calcifications in the samples.

Figure 11:
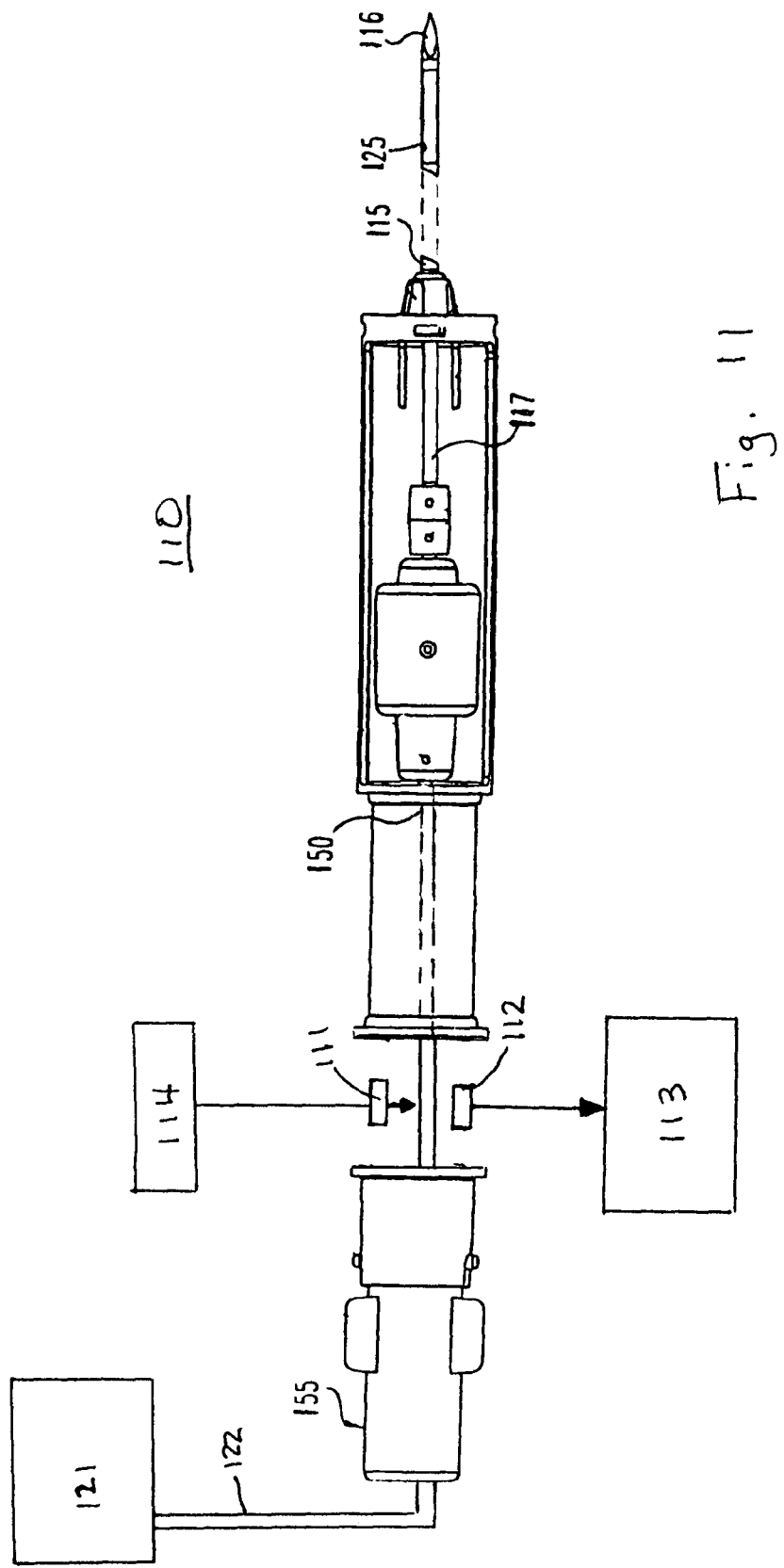

In one example (FIG. 11), a tissue biopsy apparatus 110 configured as a handheld device (although the apparatus can also be mounted to a support fixture that is used to position the biopsy needle) includes a biopsy needle mounted to a handpiece. The biopsy needle includes an outer cannula 115 terminating in a tip 116. A tissue-receiving opening 125 is provided (relatively) near the tip 116. An inner cannula 117 fits concentrically within the outer lumen of the outer cannula 115. The inner cannula 117 is rotated (for example, by a rotary motor) about its longitudinal axis and is translated axially within the outer cannula 115 (for example, by a reciprocating motor drive). The outer cannula 115 terminating, tip 116, inner cannula 117 and tissue-receiving opening 125 interoperate similar to the other examples discussed above to extract biopsy samples of a patient's breast. The inner cannula 117 provides an avenue for aspiration of the biopsy samples to the tissue aspiration path which also includes aspiration tube 150 coupling the tissue aspiration path to a collection chamber 155. Aspirator 121 applied vacuum or aspiration pressure to the collection chamber to draw samples through the tissue aspiration path to the collection chamber 155. X-ray tube 111 and detector 112 operate under appropriate control of a controller 114, and a detection signal representing the x-rays received by the detector 112 from the source 111 is output to CAD component 113 which decodes the signal to determine whether the samples include calcifications and estimates an amount of the calcifications. CAD systems and techniques are well-known in the art, and therefore a detailed discussion of such systems and techniques is omitted from this disclosure in the interest of clarity and brevity.

In the case that the collection filter is integrated with the biopsy needle in a handheld device or in a needle stage, the x-ray tube and detector would be small-scaled. An example of a small scale detector is available from Hamamatsu, Corporation, 10 Bridgewater, N.J. Information regarding a small scale x-ray tube (40 kV metal-ceramic X-ray tube) is available from Newton Scientific Inc., Cambridge, Mass.

In addition, an additional line 106 can be added for introducing anesthetic and/or contrast agents, for example, along with a flushing agent or lavage. The introduction of the anesthetic and/or contrast agents can be automated and synchronized to the imaging sequence.

Figure 12:
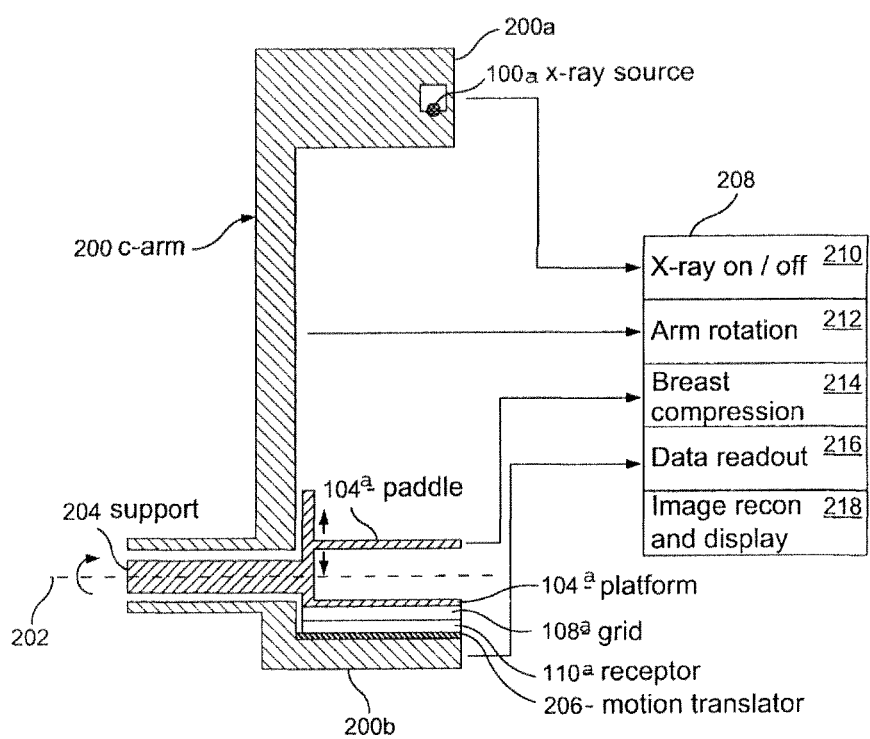

FIG. 12 schematically illustrates a side view of a system comprising x-ray source 100a at one end 200a of a C-arm 200 that is supported for selective rotation about an axis 202, independently of a support 204 for compression paddle 104a and breast platform 106a. Support 204 also selectively rotates about the same axis 202. The other end 200b of C-arm 200 interacts with x-ray receptor 110a through a motion translator schematically illustrated at 206 that translates the rotational motion of the end 200b about axis 202 to a substantially translational motion of receptor 110a that substantially maintains the distance of receptor 110a from breast platform 106a while x-ray data is being taken. FIG. 2 is not to scale, and receptor 110a can be spaced further from member 200b than illustrated, to allow more space for motion translator 206, and also to allow for receptor 110a to be moved selectively further from or closer to breast platform 104a and thus allow for x-ray image magnification. In operation, C-arm 200 and support 204 are rotated to desired angular positions, either manually or by motor drives, patient breast 102a is positioned on platform 106a and is immobilized by bringing paddle 104a toward platform 106a and compressing breast 102a, with typically the same or less force than for a typical conventional mammogram, such as between one to one-third the conventional force. With breast 102a immobilized, and with C-arm at a selected angle relative to a normal to platform 106a and receptor 110a, such as +15°, imaging starts, and a projection image is taken for each of a number of selected angular positions of source 100a while C-arm 200 rotates, continuously or intermittently, through a selected angle, such as an angle of 30°, i.e. from +15° to −15°. Of course, the motion can be in the opposite direction, from −15° to +15°, or can be over a different angular interval, such as over less than a total of 30°, e.g. 25°, 20°, etc., or more than 30° such as 35°, 40°, etc. Currently, the preferred is ±15°. A set of image data can be taken at selected angular positions, such as every degree, or every fraction of a degree, or every several degrees of angle. The angular increments between the different positions for sets of image data need not be the same. For example, the increments around 0° can be less hose at the extremes of the angular positions, or vice versa. Currently, the preferred angular increment is 3°. The sets of image data can be taken after an incremental motion from one angular position of source 100a to another, and from one translational position of receptor 110a to another, such that source 100a and receptor 110a are stationary while a set of image data is being taken. Alternatively, one or both of source 100a and receptor 110a can move continuously while sets of image data are being taken, one set for each increment of continuous motion. In the currently preferred embodiment, in the example of continuous motion while taking image data both source 100a and receptor 110a move while image data are being taken.

FIG. 12 also illustrates schematically an electrical/electronic system 208 that interacts with the components discussed above. System 208 includes a control 210 for selectively energizing and otherwise controlling x-ray source 100a, an arm rotation control 212 for selectively rotating C-arm 200 and support 204, a breast compression control 214 for selectively moving compression paddle 104a toward and away from breast platform 106a, data readout electronics 216 coupled with x-ray receptor 110a to read out the sets of image data at the respective positions of source 100a and receptor 110a relative to immobilized breast 102a, and an image reconstruction and display unit 218 coupled with data readout electronics 216 to receive the sets of image data from electronics 216 and to process the image data for reconstruction and other purposes and display images.

For a given position of breast 102a, such as a position that is the same or similar to the CC position for a conventional mammogram, source 100a and receptor 110a can be positioned relative to immobilized breast 102a such that at the 0° position a center ray of the x-ray beam from source 100a would be substantially normal to receptor breast platform 106a and receptor 110a. For a first set of image data, source 100a is at + (or −) 15° in a preferred example and is) gradually moved, continuously or intermittently to − (or +) 15°, with a set of image data taken every 3°. The angular range and the increment over which data sets are taken can each be selectively set by the operator, depending of characteristics of the breast being imaged and the screening and diagnostic needs, and can be different for different patients or from one to the other breast of the same patient. For example the source can move through angles that range from a fraction to a degree to several degrees from one imaging position to the next. Each set of image data is supplied by image readout 216 for processing at image reconstruction and display unit 218. Each set of image data can be taken at the same x-ray dose to the breast, and the dose at any one of the different imaging positions can be substantially less than that for a conventional mammogram. The x-ray dose can be substantially the same for each imaging position, but preferably the dose at one of the position, e.g., at or close to the 0° position, is the same or similar to dose for a conventional mammogram while the dose at the each of the other positions is less, preferably much less. Alternatively, the scan can begin with or end with an exposure close to the 0° position at a dose similar to a conventional mammogram, and the rest of the set of image data can be over the angular range with each exposure at an x-ray dose that is substantially less than that for a conventional mammogram. Thus, two types of images can be produced in accordance with the currently preferred embodiment while breast 102a is immobilized in the same position. One type is the same or is at least similar to a conventional mammogram which can be read and interpreted in the manner familiar to health professionals. The other type is tomosynthetic images reconstructed from the image data and displayed either separately or as an adjunct to the display of the image that the same or similar to a conventional mammogram. The process described above or one position of breast 102a can be repeated for another position. For example one process can be for a breast position in a manner that is the same or similar to positioning the breast for a conventional CC view, the breast can then be released, the support 204 and C-arm 200 rotated to other angular positions and the breast repositioned in a manner that is the same and similar to the position for an MLO view, and the procedure repeated.

An alternative embodiment, illustrated schematically in a front view in FIG. 13 and in side view in FIG. 14, is similar except that receptor 110a is affixed to the end 200b of C-arm 200 that is opposite x-ray source 100a. In this embodiment, receptor 110a moves relative to immobilized breast 102a along an arcuate path from one imaging position to another. Because the change in angle between receptor 110a and breast platform is small, it can be disregarded in processing the sets of x-ray image data. Alternatively, a geometric correction known to those skilled in the art can be applied to each set of image data to convert it to interpolated pixel values that would correspond to those that would have been obtained if receptor 110a had been parallel to and at the same distance from platform 106a at all imaging positions. The so corrected sets of image data can then be used in filtered back projections as described above.

Figure 15:
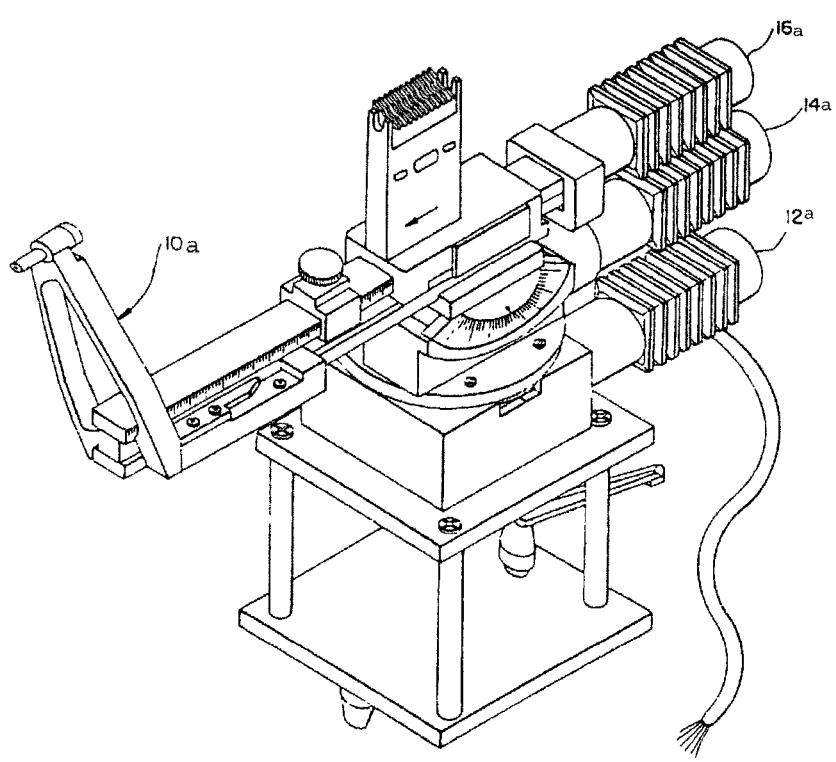
FIGS. 15-18 illustrate a biopsy stage and its operation.

FIG. 15 illustrates a biopsy needle positioning mechanism that is typically employed as a component of an overall mammographic needle biopsy system, and comprises a conventional puncture instrument 10a for retaining a biopsy needle or other biopsy or therapeutic delivery device (not illustrated). Three conventional DC motors 12a, 14a, and 16a are provided for moving the biopsy needle retained by the puncture instrument 10a in the rotation and angulation axes and for setting a stop position along the depth axis, respectively. Positional feedback is provided to the biopsy needle positioning motor controller by the three DC motors 12a, 14a, and 16a. The operator hand controller allows the clinician user to control the motorized biopsy needle positioning system. Controls are provided to permit the user to initiate movement of the biopsy needle into a position for insertion to the identified point of interest within the patient's breast, in accordance with the computed spatial coordinates of that point of interest. The position of the biopsy needle may be monitored by the user with reference to a 32-character display on the operator hand controller. An enable switch is provided to prevent inadvertent motion of the biopsy needle.

The remote view and display box receives the spatial coordinates of rotation, angulation, and depth from the biopsy needle positioning motor controller and displays them for the benefit of the clinician user or others on a 40-character alphanumeric display. The remote view and display box may be conveniently mounted on a table that includes means for mounting and lighting x-ray reference films to be viewed during a breast biopsy procedure.

Figure 16:
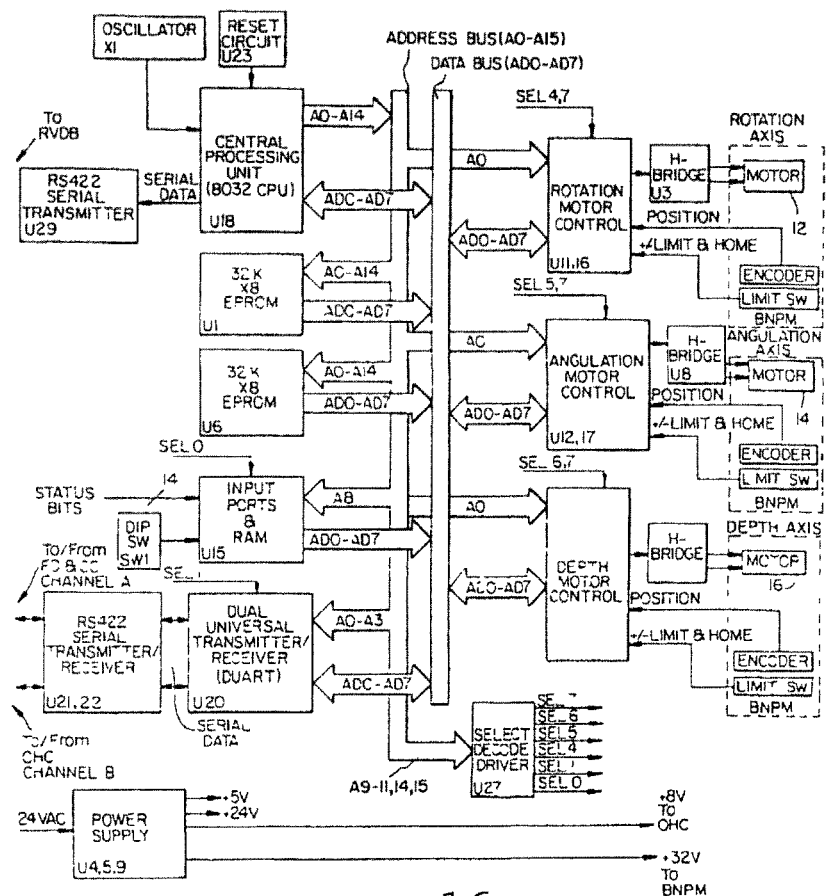

Operation of the biopsy needle positioning motor controller may be understood with reference to the detailed block diagram of FIG. 16. The biopsy needle positioning motor controller receives the spatial coordinates of the identified point of interest within the patient's breast from the film digitizer and coordinates calculator and computes the variables required to drive the three DC motors 12a, 14a, and 16a that form part of the biopsy needle positioning mechanism. Information regarding the position of the biopsy needle is continuously provided by the biopsy needle positioning motor controller to the LED displays in the operator hand controller. During manual operation, the biopsy needle positioning motor controller receives commands from the operator hand controller and drives the biopsy needle positioning mechanism in the direction specified for as long as the user simultaneously depresses one of the direction arrow keys and the enable switch located on the operator hand controller illustrated in FIG. 17.

A central processing unit (8032 CPU) within the biopsy needle positioning motor controller has a direct serial communications link with the remote view and display box through an RS422 serial transmitter U29. The 8032 CPU also has two bi-directional communications links through a dual synchronous universal transmitter/receiver DUART, which provides serial communications between the biopsy needle positioning motor controller and both the film digitizer and coordinates calculator (serial channel B) and the operator hand controller (serial channel A).

Under normal operating conditions, the 8032 CPU loads the three DC motor controller sections (rotation, angulation, and depth) with high level initial conditions data. This initial conditions data includes velocity constants, acceleration constants, PID filter information, and sample period. When the spatial coordinates of the identified point of interest within the patient's breast, as computed by the film digitizer and coordinates calculator, are placed on the data bus ADO-AD7 by DUART U11, the 8032 CPU reads these spatial coordinates and calculates the corresponding motor control values. The 8032 CPU then sends this data to the three motor control sections. The motor control sections calculate the actual motor drive voltages and provide the drive voltages to motors 12a, 14a, and 16a through separate H-bridge circuits. The motor control sections monitor the encoder feedback from the biopsy needle positioning mechanism to determine the position of the biopsy needle and to adjust the motor drive voltages as the biopsy needle reaches the identified point of interest. A typical motor voltage and velocity profile is trapezoidal in nature, ramping up to a start voltage, then holding constant, and finally ramping down to a stop voltage when the biopsy needle has reached the position required for insertion to the identified point of interest.

The 8032 CPU support circuits include operating and debug program data in erasable programmable read-only memories EPROMs U1 and U6. Fourteen status bits plus a six-bit DIP switch are monitored through an input port and a random access memory RAM 1115. The status bits include +/−limit switches and a home switch associated with each coordinate axis. Two additional status bits serve to monitor the +5-volt (+5ENC) and +24-volt (+24VOK) power supplies. A reset circuit U23 provides a reset signal to reset the 8032 CPU when power is initially applied. The reset circuit also monitors program execution by counting a pulse associated with each cycle of the program and by executing a CPU reset command if the pulses stop, as may occur during a software lockup.

Figure 17:
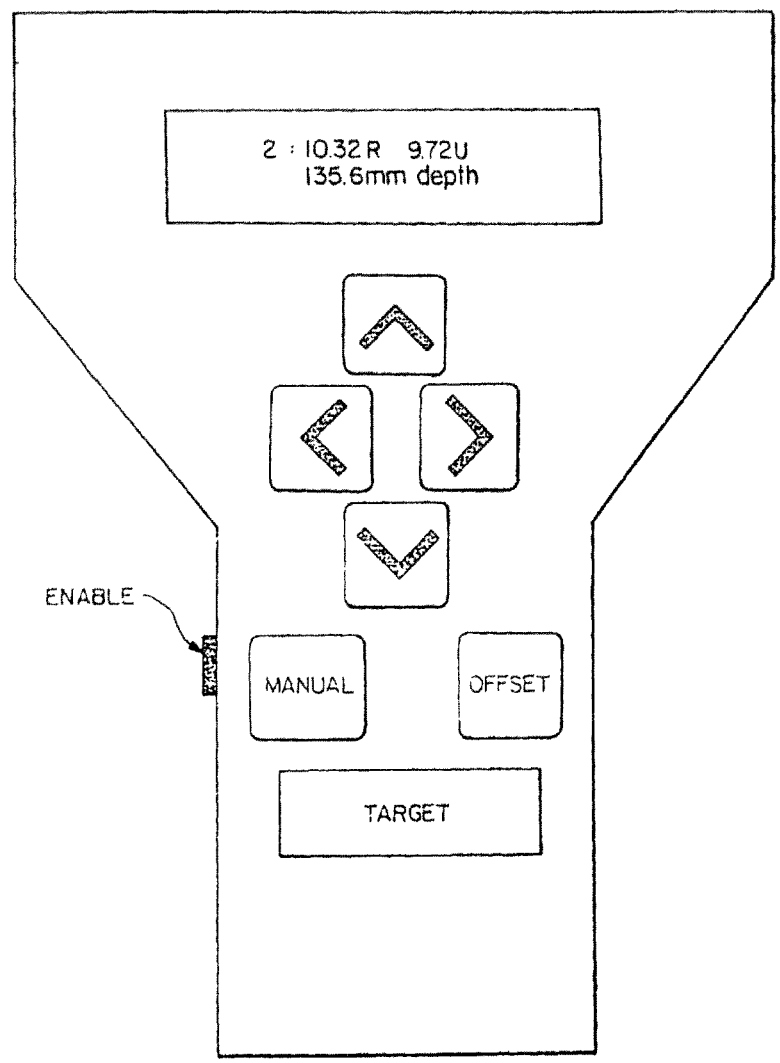
Figure 18:
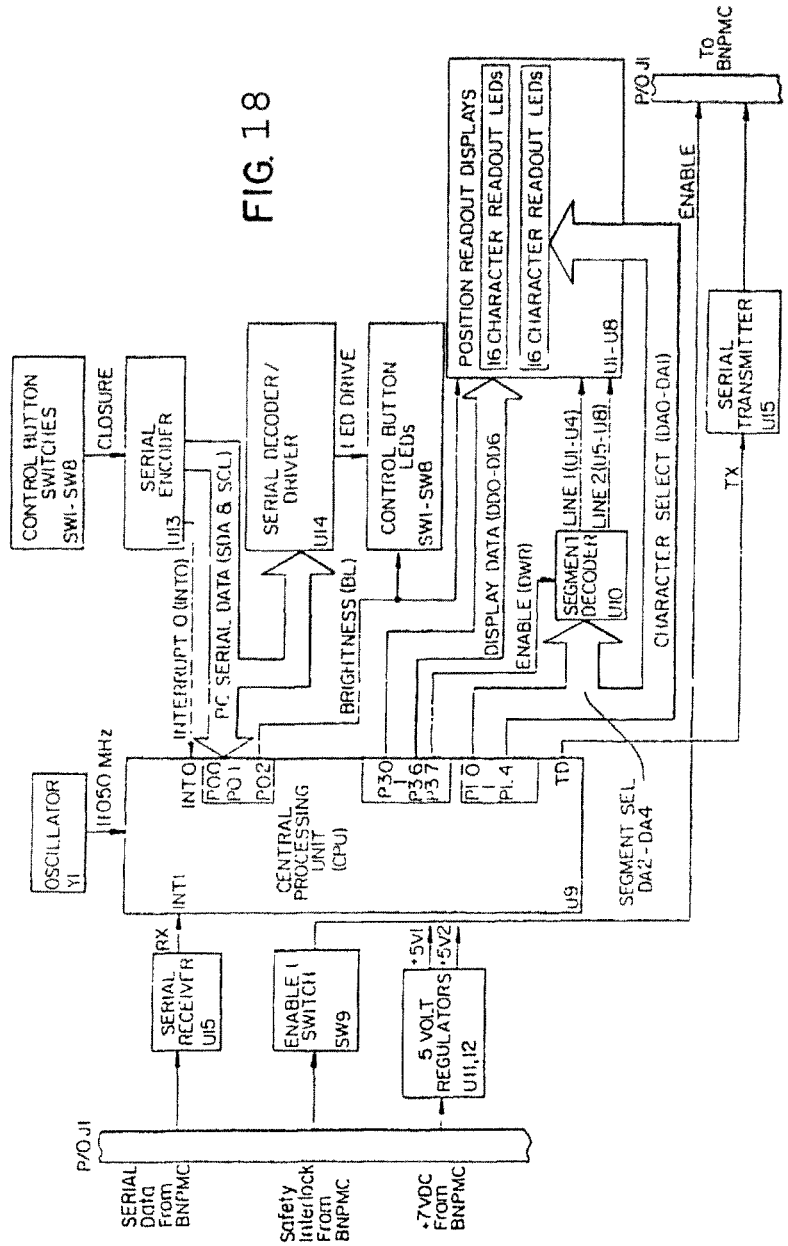

Referring now to FIGS. 17 and 18, it will be understood how the operator hand controller of FIG. 17 transmits data to and receives data and instructions from the biopsy needle positioning motor controller via an RS422 serial transmitter/receiver bus (serial channel A). While the operator hand controller described herein as being a hand-held unit, it may also comprise a console or table-mounted unit. The principal functions of the operator hand controller are to 1) transmit switch closure data resulting from actuation of the direction arrow keys and the MANUAL, OFFSET, and TARGET keys to the biopsy needle positioning motor controller; 2) illuminate button LEDs in accordance with information received from the biopsy needle positioning motor controller; and 3) display the spatial coordinates of the identified point of interest within the patient's breast, as provided by the biopsy needle positioning motor controller. Additionally, the operator hand controller provides a safety interlock through the ENABLE switch SW9, which must be simultaneously depressed by the user with a selected one of the function keys in order to initiate any of the functions of the operator hand controller. The ENABLE switch is mounted on the side of the operator hand controller and, when depressed, energizes a relay in the biopsy needle positioning motor controller that enables movement of the biopsy needle positioning mechanism. When this switch opens, the relay removes power from the three DC motors 12a, 14a, and 16a of the biopsy needle positioning mechanism.

The clinician user initiates control of the biopsy needle positioning mechanism in either an automatic or manual mode by depressing control switches on the operator hand controller. Depressing one of the arrow keys or one of the MANUAL, OFFSET or TARGET keys has the effect of grounding a corresponding input of serial encoder U13. This causes serial encoder U13 to apply an INTERRUPT 0 (INTOO) to the CPU U9 and place the serial data in 12C protocol on the serial lines SDA and SCL to the CPU U9. The CPU U9 converts the switch information to RS422 protocol and sends it to the biopsy needle positioning motor controller via serial transmitter U15. Each of the keys on the operator hand controller contains a light emitting diode LED that is illuminated under the control of the biopsy needle positioning motor controller. The biopsy needle positioning motor controller selects a particular LED to be illuminated, sets the brightness of that LED, and determines how long that LED is to remain illuminated. This information is sent to the CPU U9 via serial receiver U15. The CPU U9 then places the information in 12C protocol on the serial lines SDA and SCL to be transmitted to serial decoder/driver U14. Ser. decoder/driver U14 pulls a corresponding output to its low state, thereby illuminating the selected LED. The CPU U9 controls the brightness of the LEDs on the operator hand controller by setting the duty cycle of BRIGHTNESS (BL) pulses applied to the LEDS. A 50% duty cycle illuminates the LEDs at half brightness and a 100% duty cycle illuminates the LEDs at full brightness.

The position readout displays U1-U8 in the operator hand controller provide two rows of displayed information comprising 16 ASCII characters in each row. Each row comprises four display devices, and each display device contains four 5.times.7 dot matrix character displays. Referring to FIG. 4, the top line of the position readout display indicates target number 2 (2:), a rotation axis angle of 10.32 degrees right (10.32R), and an angulation axis angle of 9.72 degrees up (9.72U). The bottom line of the position readout display indicates a depth stop setting of 135.6 millimeters (135.6 mm depth). As previously described in connection with LEDs that illuminate each of the keys of the operator hand controller, the biopsy needle positioning motor controller similarly controls the position readout displays through serial communications with the operator hand controller CPU U9. The CPU U9 provides segment selection control and character display using two data buses DD0-DD7 and DA0-DA4. To display a selected ASCII character, the CPU U9 puts data describing the character on the DD0-DD7 (P3.0-P3.6 outputs of the CPU U9) bus. The CPU U9 transmits a low signal FNABLE (DWR) to segment decoder U10, which decodes bits DA2-DA4 and applies a low enable signal to the appropriate ones of display device U1-U8. The enabled display device then decodes the character select bit DA0 and DA1 to select the character position which displays the ASCII character defined by data bus DD0-DD6. As with the LEDs, the biopsy needle positioning motor controller defines the brightness of the position readout display. The biopsy needle positioning motor controller communicates the brightness level to the CPU U9, which then switches the BRIGHTNESS (BL) signal on and off, producing the designated duty cycle.

Many variations can be introduced on the above-discussed illustrative embodiments and examples without departing from the spirit of the disclosure or from the scope of the appended claims. For example, elements and/or features of different examples and illustrative embodiments may be combined with each other and/or substituted for each other within the scope of this disclosure and appended claims.

What is claimed is:

1. A system for facilitating biopsy needle localization utilizing tomosynthesis imaging of a patient's breast comprising:
   a breast platform configured to support a patient's breast for x-ray imaging and a biopsy needle assembly with a breast biopsy needle;
   a computer having a program stored thereon configured to receive image data acquired with an x-ray image receptor while an x-ray source moves through a multiplicity of image positions along a source trajectory and irradiates the receptor with an imaging x-ray beam from at least three of said imaging positions after the beam passes through the patient's breast in the course of a tomosynthesis scan;
   wherein at least a portion of said needle assembly is between at least some of said imaging positions of the x-ray source and the patient's breast on said platform;
   said computer being further configured to computer-process said image data to obtain (i) at least three tomosynthesis projection images of the breast taken at different angles of the source relative to the breast platform and (ii) a plurality of reconstructed tomosynthesis slice images representing respective slices of the patient's breast;
   said computer being further configured to counter effects on said tomosynthesis images due to at least a portion of said needle assembly being between at least some of said multiplicity of imaging positions of the x-ray source and the patient's breast by avoiding or reducing use, in said tomosynthesis images, of image data for said at least some of said multiplicity of imaging positions; and
   a user interface configured to receive said tomosynthesis images from said image forming unit and display said tomosynthesis projection images and said reconstructed tomosynthesis slice images, receive identification of an area of interest inside the patient's breast as imaged in at least one of said tomosynthesis images, and determine therefrom three-dimensional coordinates of the identified area of interest in the breast;
   wherein said biopsy needle is positioned based on said three-dimensional coordinates of said area of interest in the breast.

2. The system of claim 1, wherein said computer is configured to process into said tomosynthesis images only image data acquired from image positions of the x-ray source in which said needle assembly is not casting an x-ray shadow in said area of interest during said tomosynthesis scan.

3. The system of claim 1, wherein said user interface is configured to record a mark for said identification of the area of interest in the patient's breast on at least one of the tomosynthesis images, and to automatically place a mark at a corresponding location on one or more other tomosynthesis images of the patient's breast.

4. The system of claim 1, wherein said computer is configured to obtain one or more pre-fire images of the patient's breast for verifying needle location relative to said area of interest while at least a portion of said needle assembly is between at least some of said imaging positions and the breast but prior to a firing of said biopsy needle into the patient's breast.

5. The system of claim 1, wherein said computer is configured to obtain a post-fire image for verifying proper needle location, after a firing of said biopsy needle into the patient's breast but before tissue of the patient's breast is sampled.

6. The system of claim 1, wherein the biopsy needle is radiolucent, with the needle tip being radio-opaque.

7. The system of claim 1, wherein the needle assembly further includes an introducer, and the introducer is radiolucent, with a radio opaque band at a distant end of the introducer.

8. The system of claim 1, wherein a body of the needle assembly is radiolucent, with the needle tip being radio-opaque.

9. The system of claim 1 further comprising:
   a positioning device coupled to said needle assembly;
   and a biopsy controlling computer;
   wherein said positioning device is motorized, and said biopsy controlling computer controls said motorized positioning device to move said needle to a specific position based on said three-dimensional coordinates determined by said user interface.

10. The system of claim 9, wherein said biopsy controlling computer is configured to control said motorized positioning device to move said needle prior to said tomosynthesis scan, to a non-interfering position where the needle does not cast x-ray shadow in said area of interest during said tomosynthesis scan while the x-ray source is at least at some of said imaging positions.

11. The system claim 1, wherein said three-dimensional coordinates of said area of interest are displayed via said user interface, and needle tip coordinates are dynamically displayed via said user interface as the biopsy needle is manually positioned.

12. The system of claim 1 further comprising:
a biopsy needle positioning mechanism coupled to said needle assembly to move said needle assembly and configured for an operator to manually position the needle relative to the patient's breast utilizing the biopsy needle positioning mechanism.

13. The system of claim 12 further comprising:
An hand operated device coupled mechanically or electrically to said biopsy needle positioning mechanism and configured for an operator to manually operate said hand operated controller to control the biopsy needle positioning mechanism to position the needle relative to the patient's breast.

14. The system of claim 1 further comprising:
a collection chamber configured to collect samples obtained by the biopsy needle, and a delivery path through which said samples pass from the biopsy needle to the collection chamber; and
an automated calcification detector coupled with said delivery path between said biopsy needle and said collection chamber,
wherein said automated calcification detector determines, as said samples are moving through said delivery path, whether the samples passing through said path include calcifications.

15. The system of claim 14, wherein said automated calcification detector is configured to estimate an amount of said calcifications.

16. The system of claim 1 further comprising:
an additional line coupled to the needle assembly for introducing anesthetic and/or contrast agents into the patient's breast,
wherein the introduction of the anesthetic and/or contrast agents is synchronized to said tomosynthesis scan.

17. The system of claim 1, wherein the image forming unit is configured to reconstruct said tomosynthesis slice images using filtered back projection.

18. The system of claim 1, wherein the image forming unit is configured to reconstruct said slice images uses artifact reduction methods.

19. A method for needle localization for breast biopsy, said method comprising the steps of:
(a) performing a tomosynthesis scan of a patient's breast using a source of an imaging x-ray beam that moves through a multiplicity of imaging positions along a source trajectory, and obtaining image data from said tomosynthesis scan and deriving therefrom (i) tomosynthesis projection images of the breast taken from more than two of said imaging positions of the source relative to the breast and (ii) tomosynthesis reconstructed slice images representing respective slices of the breast;
(b) displaying at least some of said tomosynthesis ages of the patient's breast;
(c) receiving an indication on at least some of said tomosynthesis images of an area of interest within said patient's breast, and determining therefrom three-dimensional coordinates of said area of interest; and
(d) positioning a biopsy needle based on said three-dimensional coordinates of said area of interest determined in step (c);
(e) wherein said determining of coordinates of the area of interest comprises countering effects of the biopsy needle shadowing the breast due to the needle being between the source and the breast for at least some of said multiplicity of imaging positions of the source by avoiding or reducing use, in said tomosynthesis images, of image data for said at least some of said multiplicity of imaging positions.

20. The method of claim 19, further comprising:
positioning said biopsy needle prior to step (a) at a non-interfering position for at least some of said imaging positions of the source of the imaging x-ray beam such that the biopsy needle is not shadowing said area of interest during said tomosynthesis scan.

21. The method of claim 20, further comprising:
positioning said biopsy needle with a motorized stage prior to step (a) to counter casting an x-ray shadow of the needle in said area of interest during said tomosynthesis scan.

22. The method of claim 19, further comprising:
(f) inserting said biopsy needle into the patient's breast after step e;
(g) applying X-ray exposures to obtain one or more pre-fire images of the patient's breast for verifying needle location relative to said area of interest determined in step c;
(h) firing said biopsy needle, after verifying the needle location by obtaining one or more post-fire images using said imaging x-ray beam; and
(i) said obtaining of one or more post-fire images for verifying proper needle location, taking place before tissue of the patient's breast is sampled.

23. The method of claim 22, further comprising:
recording said area of interest in the patient's breast as a mark on one or more of the tomosynthesis images.

24. The method of claim 23, further comprising:
placing the mark at a corresponding location on at least one of one or more pre-fire images and post-fire image of the patient's breast.

25. The method of claim 19, wherein said needle is between the source and the area of interest in the breast for a first set of said imaging position but not for a second set of the imaging positions, and wherein said tomosynthesis scan is performed in step (a) with imaging x-ray beams only from the second set of imaging positions.

26. The method of claim 19, further comprising:
allowing the biopsy needle to be positioned at a test position a selected distance from the area of interest;
imaging the patient's breast with the biopsy needle positioned at the selected distance from the area of interest, and generating a verification image based on data acquired from said imaging;
indexing the biopsy needle from said test position to a specific position within the area of interest, after receiving confirmation that the area of interest is not obscured by the biopsy needle in the verification image, and performing at least one additional breast imaging operation.

27. The method of claim 19, further comprising:
displaying said three-dimensional coordinates of said area of allowing the biopsy needle to be manually positioned; and
dynamically displaying needle tip coordinates as the biopsy needle is manually positioned.

28. The method of claim 19, further comprising:
determining a volume of said area of interest; and
displaying said volume of said area of interest.

29. The method of claim 19, where the needle positioning in step (d) is via a motorized mechanism.

30. The method of claim 19, wherein the needle positioning in step (d) is performed manually.

31. The method of claim 19, wherein the needle positioning in step (d) is performed by operating a hand-operated device.

32. An apparatus for performing breast biopsy, comprising:
- a biopsy needle configured to obtain samples of a patient's breast;
- a collection chamber coupled to the biopsy needle via a sample delivery path through which samples of the patient's breast obtained with said biopsy needle are delivered to said collection chamber; and
- a calcification detector coupled to the sample delivery path and configured to determine, as the samples are passing through said sample delivery path on their way to the collection chamber, whether the samples include calcifications and to estimate an amount of the calcifications.

* * * * *